US009642774B2

(12) United States Patent
Sattig

(10) Patent No.: US 9,642,774 B2
(45) Date of Patent: May 9, 2017

(54) LIQUID CONTAINER WITH PREDETERMINED BREAKING POINT

(75) Inventor: Christoph Helmut Sattig, Dieburg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 43 days.

(21) Appl. No.: 14/343,618

(22) PCT Filed: Sep. 7, 2012

(86) PCT No.: PCT/EP2012/003762

§ 371 (c)(1), (2), (4) Date: Mar. 7, 2014

(87) PCT Pub. No.: WO2013/034302

PCT Pub. Date: Mar. 14, 2013

(65) Prior Publication Data

US 2014/0202980 A1 Jul. 24, 2014

(30) Foreign Application Priority Data

Sep. 7, 2011 (DE) ........................ 10 2011 112 516

(51) Int. Cl.

*A61B 19/00* (2006.01)
*A61J 1/06* (2006.01)
(Continued)

(52) U.S. Cl.

CPC ................ *A61J 1/065* (2013.01); *A61J 1/05* (2013.01); *A61J 1/1406* (2013.01); *A61J 1/20* (2013.01); *A61J 1/1468* (2015.05)

(58) Field of Classification Search

CPC ...... A61J 3/06; A61J 3/10; A61J 1/201; A61J 1/2096; A61J 1/2075; A61J 1/2082;
(Continued)

(56) References Cited

U.S. PATENT DOCUMENTS 1,680,616 A 8/1928 Horst
1,744,893 A 1/1930 Hein
(Continued)

FOREIGN PATENT DOCUMENTS

DE 60012383 T2 9/2005
DE 69634704 T2 3/2006
(Continued)

OTHER PUBLICATIONS

International Search Report dated Apr. 8, 2012 in PCT/EP2012/003762.

(Continued)

*Primary Examiner* — Leslie Deak
(74) *Attorney, Agent, or Firm* — Lerner, David, Littenberg, Krumholz & Mentlik, LLP

(57) ABSTRACT

Liquid container with a predetermined break point (4), which is covered by an elastomer septum (3). The container forms a hollow body (10) made of a single material that is compatible with critical liquids such as medicines. The elastomer septum (3) and the predetermined break point (4) can be pierced by a hollow needle (51) in order to withdraw liquid from the container.

21 Claims, 3 Drawing Sheets

Figure 1:
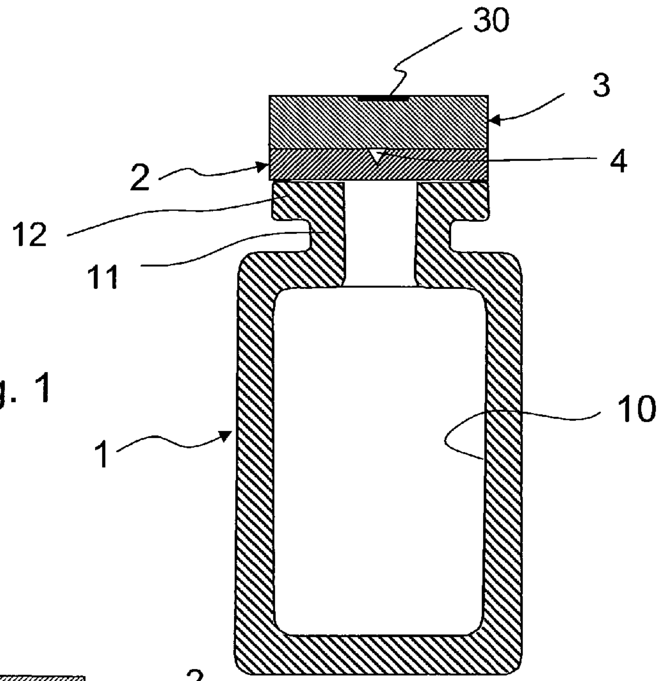

(51) Int. Cl.
*A61J 1/05* (2006.01)
*A61J 1/14* (2006.01)
*A61J 1/20* (2006.01)

(58) Field of Classification Search
CPC A61J 1/10; A61J 1/1406; A61J 1/2089; A61J 2001/201; A61J 604/405; A61J 604/415; A61J 1/2055; A61J 1/2065; A61J 1/2072; A61J 1/1412; A61J 1/2079; A61J 1/065; A61J 1/05; A61J 1/406; A61J 1/1468
USPC .......................................... 604/405, 411, 415
See application file for complete search history.

(56) References Cited

U.S. PATENT DOCUMENTS 2,425,093 A 8/1947 Fosler
2,638,022 A 5/1953 Reyes
3,036,819 A 5/1962 Edwin
3,228,565 A 1/1966 Stanzel
3,506,006 A 4/1970 Lange, Jr.
3,654,926 A * 4/1972 Rietman ............... A61J 1/2093 604/416
3,739,947 A 6/1973 Baumann et al.
3,742,988 A 7/1973 Kush
3,869,315 A 3/1975 Dolgner
3,872,867 A 3/1975 Killinger
3,892,237 A 7/1975 Steiner
3,945,382 A 3/1976 Ogle
3,983,994 A 10/1976 Wyslotsky
3,986,838 A 10/1976 Reichert
3,995,630 A 12/1976 van de Veerdonk et al.
4,043,335 A 8/1977 Ishikawa
4,178,928 A 12/1979 Tischlinger
4,180,070 A 12/1979 Genese
4,185,582 A 1/1980 Bryant
4,218,525 A 8/1980 Selgin
4,227,528 A 10/1980 Wardlaw
4,241,850 A 12/1980 Speer et al.
4,246,229 A 1/1981 McBride et al.
4,272,479 A 6/1981 Huneke et al.
4,298,777 A 11/1981 Bryant
4,306,554 A 12/1981 Schwartz et al.
4,312,344 A 1/1982 Nilson
4,328,754 A 5/1982 Goodman
4,340,007 A 7/1982 Hogan
4,375,504 A 3/1983 Jensen et al.
4,423,724 A 1/1984 Young
4,453,934 A 6/1984 Gahwiler et al.
4,463,875 A 8/1984 Tepic
4,465,183 A 8/1984 Saito et al.
4,467,588 A 8/1984 Carveth
4,483,049 A 11/1984 Gustavsson et al.
4,505,433 A 3/1985 Selenke
4,515,586 A 5/1985 Mendenhall et al.
4,526,758 A 7/1985 Alengoz et al.
4,528,268 A 7/1985 Andersen et al.
4,533,641 A 8/1985 Holt
4,676,406 A 6/1987 Frischmann et al.
4,676,655 A 6/1987 Handler
4,693,706 A 9/1987 Ennis, III
4,743,229 A 5/1988 Chu
4,757,916 A 7/1988 Goncalves
4,799,801 A 1/1989 Bruning
4,801,009 A 1/1989 Amos
4,808,184 A 2/1989 Tepic
4,865,189 A 9/1989 Guerra et al.
4,936,446 A 6/1990 Lataix
4,968,302 A 11/1990 Schluter et al.
4,973,168 A 11/1990 Chan
5,051,482 A 9/1991 Tepic
5,058,770 A 10/1991 Herold et al.
5,100,241 A 3/1992 Chan
5,145,250 A 9/1992 Planck et al.
5,181,909 A 1/1993 McFarlane
5,193,907 A 3/1993 Faccioli et al.
5,252,301 A 10/1993 Nilson et al.
5,306,277 A 4/1994 Bryant et al.
5,328,262 A 7/1994 Lidgren et al.
5,330,426 A 7/1994 Kriesel et al.
5,350,372 A 9/1994 Ikeda et al.
5,393,497 A 2/1995 Haber et al.
5,435,645 A 7/1995 Faccioli et al.
5,443,182 A 8/1995 Tanaka et al.
5,501,520 A 3/1996 Lidgren et al.
5,531,683 A 7/1996 Kriesel et al.
5,545,460 A 8/1996 Tanaka et al.
5,549,380 A 8/1996 Lidgren et al.
5,564,600 A 10/1996 Renault
5,588,745 A 12/1996 Tanaka et al.
5,624,184 A 4/1997 Chan
5,628,353 A * 5/1997 Ruther ...................... B67B 7/92 141/1
5,634,714 A 6/1997 Guild
5,639,029 A 6/1997 Sundholm
5,709,668 A 1/1998 Wacks
5,779,356 A 7/1998 Chan
5,797,678 A 8/1998 Murray
5,826,713 A 10/1998 Sunago et al.
5,827,262 A 10/1998 Neftel et al.
5,876,116 A 3/1999 Barker et al.
5,879,081 A 3/1999 Chordia
5,934,803 A 8/1999 Hutter
5,948,366 A 9/1999 Ruther
5,975,751 A 11/1999 Earle
6,024,480 A 2/2000 Seaton et al.
6,027,472 A 2/2000 Kriesel et al.
6,033,105 A 3/2000 Barker et al.
6,042,262 A 3/2000 Hajianpour
6,099,532 A 8/2000 Florea
6,116,773 A 9/2000 Murray
6,120,174 A 9/2000 Hoag et al.
6,120,490 A 9/2000 Neftel
6,145,703 A 11/2000 Opperman
6,174,304 B1 1/2001 Weston
6,176,607 B1 1/2001 Hajianpour
6,210,031 B1 4/2001 Murray
6,286,670 B1 9/2001 Smith
6,312,149 B1 11/2001 Sjovall et al.
6,379,033 B1 4/2002 Murray
6,387,074 B1 5/2002 Horppu et al.
6,406,175 B1 6/2002 Marino
6,425,897 B2 7/2002 Overes et al.
6,572,256 B2 6/2003 Seaton et al.
6,598,815 B2 7/2003 Hsieh
6,626,328 B2 9/2003 Ritsche et al.
6,645,171 B1 11/2003 Robinson et al.
6,648,499 B2 11/2003 Jonsson
6,655,828 B2 12/2003 Vendrely et al.
6,682,518 B1 * 1/2004 Rothstein ................. B65D 1/09 604/411
6,706,031 B2 3/2004 Manera
6,709,149 B1 3/2004 Tepic
6,736,537 B2 5/2004 Coffeen et al.
6,743,203 B1 6/2004 Pickhard
6,755,563 B2 6/2004 Wahlig et al.
6,796,701 B2 9/2004 Wahlig et al.
6,832,703 B1 12/2004 Scott et al.
6,871,996 B2 3/2005 Jonsson
6,902,543 B1 6/2005 Cherif-Cheikh et al.
6,940,782 B2 9/2005 Matsui
6,948,522 B2 * 9/2005 Newbrough .......... A61J 1/2089 137/550
6,984,063 B2 1/2006 Barker et al.
7,018,089 B2 3/2006 Wenz et al.
7,029,163 B2 4/2006 Barker et al.
7,073,936 B1 7/2006 Jonsson
7,171,964 B2 2/2007 Moore et al.
7,311,436 B2 12/2007 Barker et al.
7,462,164 B2 12/2008 Moir
7,563,018 B2 7/2009 Wilander
7,563,245 B2 7/2009 Mu
7,621,887 B2 11/2009 Griffiths et al.
7,661,561 B2 2/2010 Ophardt et al.

(56) References Cited

U.S. PATENT DOCUMENTS

| | | | |
|---|---|---|---|
| 7,793,655 B2 | 9/2010 | Hochrainer | |
| 7,823,751 B2 | 11/2010 | Ophardt et al. | |
| 7,938,572 B2 | 5/2011 | Lidgren et al. | |
| 7,959,349 B2 | 6/2011 | Sattig et al. | |
| 7,980,754 B2 | 7/2011 | Wilander et al. | |
| 8,128,275 B2 | 3/2012 | Axelsson et al. | |
| 8,128,276 B2 | 3/2012 | Axelsson et al. | |
| 8,132,959 B2 | 3/2012 | Smit | |
| 8,256,949 B2 | 9/2012 | Melsheimer et al. | |
| 2002/0123739 A1* | 9/2002 | Haacke ................. | A61M 39/10 604/544 |
| 2003/0155381 A1 | 8/2003 | Chan | |
| 2005/0113762 A1 | 5/2005 | Kay et al. | |
| 2005/0228396 A1 | 10/2005 | Jonsson | |
| 2006/0101925 A1 | 5/2006 | Peng et al. | |
| 2009/0180349 A1 | 7/2009 | Barker et al. | |
| 2009/0264891 A1 | 10/2009 | Bogert et al. | |
| 2010/0046315 A1 | 2/2010 | Merkhan et al. | |

FOREIGN PATENT DOCUMENTS

| | | | |
|---|---|---|---|
| DE | 60126156 | T2 | 10/2007 |
| DE | 102007041666 | A1 | 4/2009 |
| EP | 0380867 | A1 | 8/1990 |
| EP | 0493363 | A2 | 7/1992 |
| EP | 0674888 | A1 | 10/1995 |
| EP | 0694498 | A1 | 1/1996 |
| EP | 0725674 | A1 | 8/1996 |
| EP | 0919215 | A1 | 6/1999 |
| EP | 1005900 | A2 | 6/2000 |
| EP | 1020167 | A2 | 7/2000 |
| EP | 1031333 | A1 | 8/2000 |
| EP | 1395208 | B1 | 1/2007 |
| EP | 1741413 | A1 | 1/2007 |
| EP | 1886648 | A1 | 2/2008 |
| EP | 1920738 | A2 | 5/2008 |
| FR | 1413976 | A | 10/1965 |
| WO | 9013264 | A1 | 11/1990 |
| WO | 9300366 | A1 | 1/1993 |
| WO | 9302322 | A1 | 2/1993 |
| WO | 9322041 | A1 | 11/1993 |
| WO | 9400415 | A1 | 1/1994 |
| WO | 9426403 | A1 | 11/1994 |
| WO | 9509641 | A1 | 4/1995 |
| WO | 9607472 | A1 | 3/1996 |
| WO | 9718031 | A1 | 5/1997 |
| WO | 9967015 | A1 | 12/1999 |
| WO | 0035506 | A1 | 6/2000 |
| WO | 0043116 | A1 | 7/2000 |
| WO | 03031042 | A1 | 4/2003 |
| WO | 2010105807 | A1 | 9/2010 |

OTHER PUBLICATIONS

International Search Report issued in PCT/EP2010/001665 and dated Jul. 20, 2010.

Written Opinion dated Apr. 8, 2012 in PCT/EP2012/003762.

* cited by examiner

LIQUID CONTAINER WITH PREDETERMINED BREAKING POINT

CROSS-REFERENCE TO RELATED APPLICATIONS

The present application is a national phase entry under 35 U.S.C. §371 of International Application No. PCT/EP2012/003762 filed Sep. 7, 2012, which claims priority from German Patent Application No. 10 2011 112 516.0 filed Sep. 7, 2011, the disclosures of which are hereby incorporated herein by reference.

The invention relates to a container for containing a liquid, a container filled with liquid, as well as a package comprising a container filled with liquid and a liquid withdrawal device.

For appropriately conserving liquid medicines, glass ampoules are used, wherein for withdrawing liquid, the ampoule head has to be broken off whereupon the content can be withdrawn by means of an injection syringe. Opening the glass ampoules is not without problems, which is the reason why containers have already been used, the cover of which consists of an elastomeric material, for example silicone or isobutyl rubber, and which is secured by means of a metallic crimp cap. Withdrawing the liquid is carried out via a hollow needle by means of which the cover wall can be pierced.

In the case of such containers with covers, there is the danger that volatile constituents can escape along the sealing surfaces or through the material itself, or that the useful liquid dissolves material constituents out of the elastomeric materials, which material constituents are undesirable in the useful liquid. Specifically in the case of medicines, all constituents of the container, even during prolonged storage, have to prove to be compatible with the liquid medicine. If substances are dissolved out of the container, they have to be toxicologically examined. The examination efforts required for this are significant.

EP 0694498 A1 and EP 0919215 A1 describe the withdrawal of a liquid from a closed glass ampoule by means of a blunt hard object, for example a thick-walled cannula. The bottom of the glass ampoule the shaft region connected thereto can be enclosed by an elastomeric part so as to retain glass splinters occurring in the ampoule region. While in the case of EP 0694498 A1, no predetermined breaking point is provided in the bottom of the glass ampoule, the bottom in the case of EP 0919215 A1, due to its shape and/or a coating, has a defined predetermined breaking point region which can be destroyed with little expenditure of force. In detail, the bottom of the ampoule has a recessed region with a point-like ceramic coating that serves as point of engagement for the opening tool of the ampoule.

It is an object of the invention to provide a liquid container that securely seals the contained liquid and avoids the danger of separating constituents from the sealing material. In comparison with glass ampoules, safe and injury-free withdrawal of liquid shall be enabled.

In order to achieve the given object, the container comprises a hollow body and an elastomer septum. Said hollow body comprises an inner wall from a single material that is compatible with the liquid. A predetermined breaking point that can be pierced with a hollow needle is provided on the hollow body. The predetermined breaking point is covered by an elastomer septum that is fixedly connected to the hollow body. In this configuration of the container, the point of the hollow needle is guided through the elastomer septum and is stabilized when piercing the predetermined breaking point. When piercing the elastomer septum, the material thereof is laterally displaced resulting in good sealing at the circumference of the hollow needle. The liquid can then be suctioned out of the container interior or can be withdrawn by generating overpressure.

The preferred material for the septum comprises silicone, isobutyl rubber and neoprene. Provided that the liquid is not in direct contact with the septum during storage, particularly inexpensive, commercially available materials can be used for the septum.

The thickness of the septum is selected in dependence on the desired degree of sealing to the hollow needle. If a very good sealing effect between the septum and the hollow needle is required, a septum thickness in the range of 3 mm is advantageous. However, if the demands on the sealing effect are lower, a thickness in the range of 1 mm can already be reasonable.

As a material for the inner wall of the hollow body, plastics or also glass can be considered.

For example, plastics from the class of polyamides, in particular PA 6.6 or PA 12, or from the class of cyclic olefin copolymers (COC), have proved to be particularly suitable for use as material for the inner wall.

Furthermore, preferably used plastics comprise the group polypropylene or polyethylene. The plastics polypropylene and polyethylene can advantageously be used for an aqueous, unproblematic liquid. Here, polypropylene is characterized, for example, by its low production costs as well as its low density and its good general material resistance with respect to various liquids.

As a glass, preferably such glass materials are used which are produced as hollow glass bodies and are suitable for pharmaceutics. Such glasses can be categorized according to their hydrolytic resistance according to ISO 719. According to this classification, glasses of the hydrolytic class 1 such as, for example, borosilicate glasses are particularly preferably used for the inner wall.

The predetermined breaking point is formed from a thickness-reduced spot of the wall of the hollow body. This thickness-reduced wall spot can be formed as a wall indentation.

The hollow body can be produced based on a jar and a cover which, after filling the container, are welded or fused together so that a gapless inner wall from a single material is formed. The use of additional filler materials and sealants can be completely dispensed with.

For withdrawing liquid, a standard needle can be used which, at its end opposite the needle point, has a customary connector to which an injection syringe for extracting the liquid can be attached. It is also possible to use a hollow needle that is supplied together with the liquid-filled container and together with the same represents a package. It is also conceivable to press the liquid out of the container by means of gas pressure.

Exemplary embodiments of the invention are described with reference to the drawings.

Figure 5:
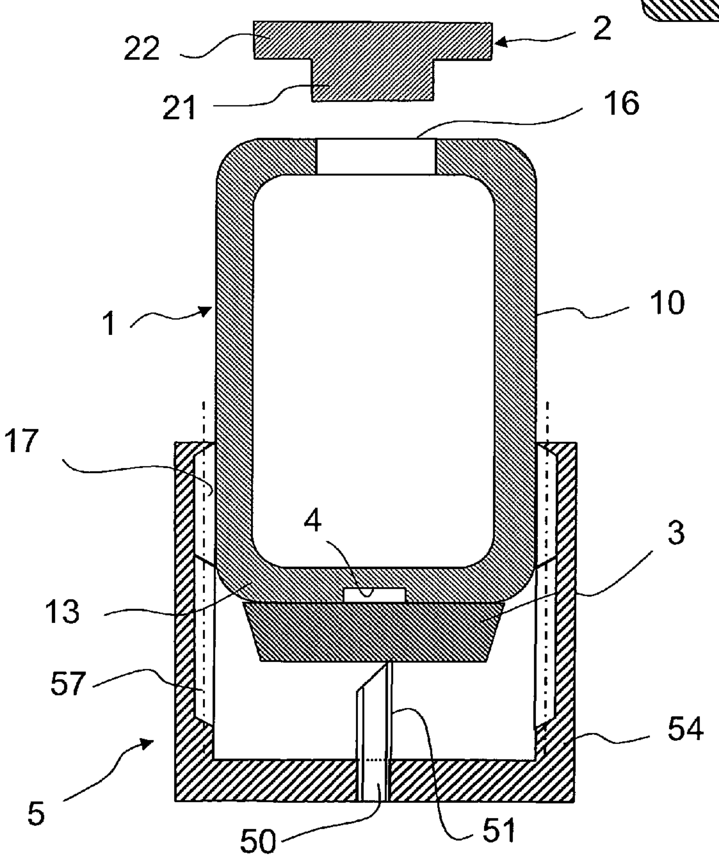
Figure 2:
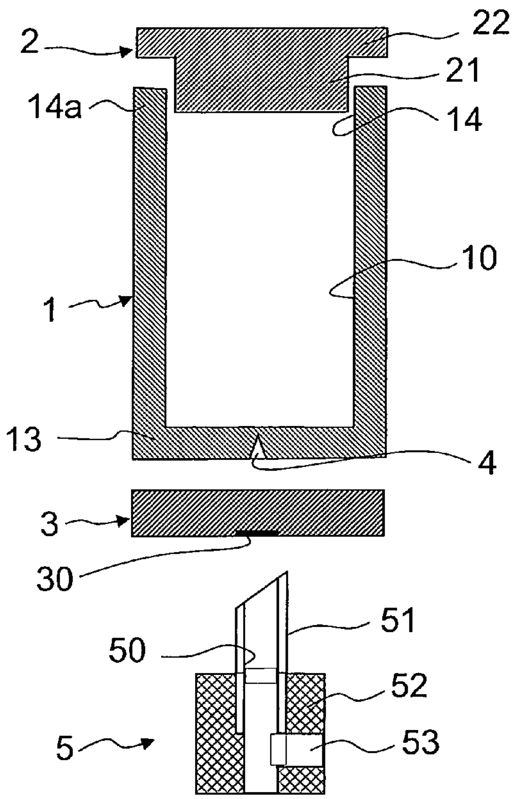
Figure 3:
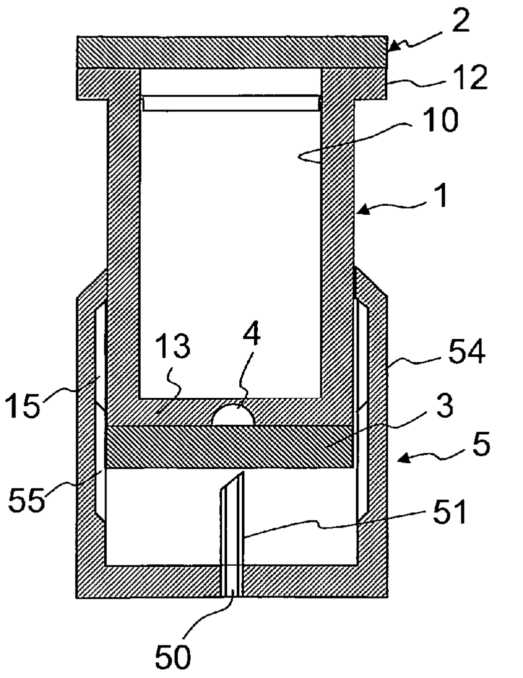
Figure 4:
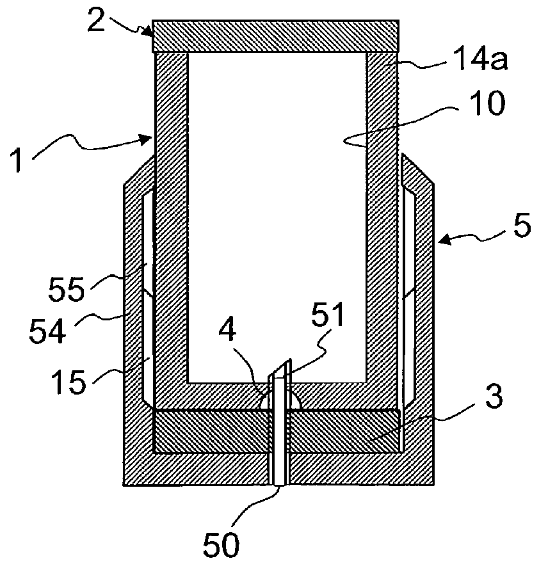
Figure 6:
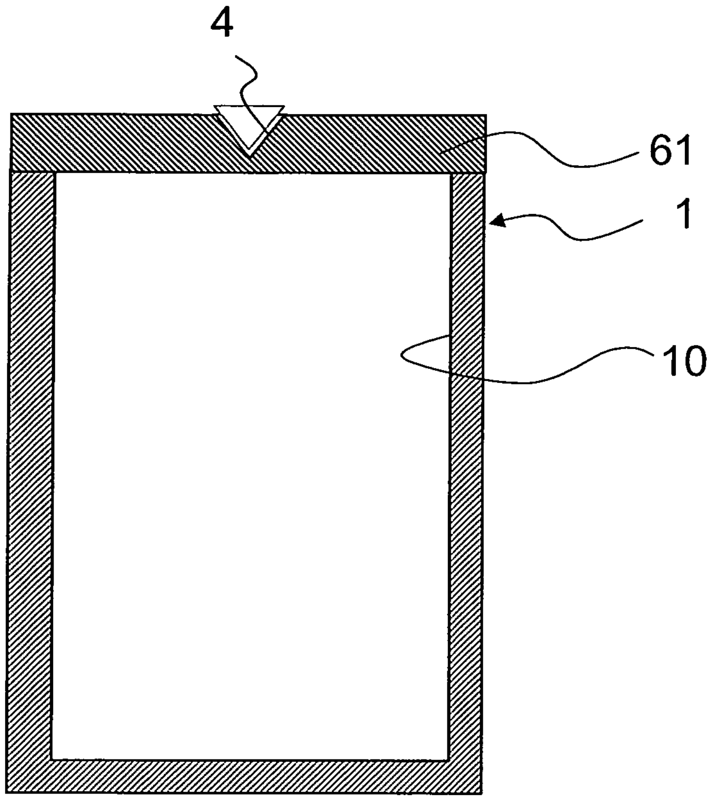

In the figures:

FIG. 1 shows a container filled with liquid and with a covered predetermined breaking point on the container cover, FIG. 2 shows individual parts of another container and a withdrawal device in an exploded view, FIG. 3 shows another configuration of a container with an attached liquid withdrawal device, FIG. 4 shows the container during withdrawal of liquid, FIG. 5 shows a container with another liquid withdrawal device, and FIG. 6 shows a container with yet another liquid withdrawal device.

FIG. 1 shows a container that is filled with liquid and comprises a hollow body 10 and a septum 3 from an elastomeric plastic. The hollow body 10 is constructed from a jar 1 and a cover 2, wherein the inner wall consists of a single material. In the cover 2, a predetermined breaking point 4 is provided. In the case of FIG. 1, the jar 1 is bottle-shaped and is formed with a neck 11 and a bottle rim 12 so as to be able to easily carry out the welding with the cover 2. This is advantageous for the glass design since the welded joint is located remote from the hollow body 10. However, it is also possible to produce it from plastic. The predetermined breaking point 4 is incorporated in the form of a funnel-shaped dent or groove in the center of the cover 2, resulting in a thickness reduction in the wall. The predetermined breaking point 4 is covered by the septum 3 that may have a mark 30 as a piercing point for the withdrawal needle. As a method for attaching the septum, adhesive bonding or injection molding on the whole can be taken into account.

FIG. 2 illustrates another possible shape of the container. The jar 1 is cylindrical and has a bottom 13 in which there is the predetermined breaking point 4. The elastomer septum 3 is secured above the predetermined breaking point on the bottom 13. After filling the interior 10 of the container, the cover 2 is inserted with its insert 21 into the jar opening 14, and the bottle rim 22 is welded together with the jar rim 14*a*. The shape of the container is suitable for production from plastic, but also from glass.

FIG. 2 also schematically illustrates a liquid withdrawal device 4 which is composed of a hollow needle 51 and a tubular body 52 that has a transverse opening 53. The hollow needle 51 and the tubular body 52 enclose a withdrawal channel 50. In the transverse opening 53, a filter can be arranged that is permeable with respect to air or other gases, but is impermeable with respect to liquids. Depending on the hardness of the container material, the hollow needle 51 consists of hard plastics or metal.

FIG. 3 shows another possible shape of the container. The jar 1 has a flanged rim 12 onto which the cover 2 is attached and secured by welding. The predetermined breaking point 4 is formed as a semi-circular dent in the bottom 13 of the jar 1. FIG. 3 further shows another embodiment of the liquid withdrawal device 5. The latter has a guide cage 54 with a plurality of guide grooves 55 which interact with guide ribs 15 on the circumference of the jar 1. The guide grooves 55 and the guide ribs 15 extend in the axial direction of the cylindrical jar 1 and thus guide the hollow needle 51 when breaking through the predetermined breaking point 4 (FIG. 4).

Apart from that, FIG. 4 shows another shape of the container having a flat cover 2 that is welded to the cylindrical rim 14*a* of the jar 1.

FIG. 5 shows another embodiment of the container and the liquid withdrawal device 5. The jar 1 is ampoule-shaped and has a relatively narrow filler opening 16 which is closed by means of a cover 2 that has an insert 21 and a bottle rim 22. The predetermined breaking point 4 is incorporated in the bottom 13 and can be formed as a cylindrical recess, as illustrated. The liquid withdrawal device 5 has a screw-cap-shaped cage 54 that is provided on the inner side with an internal thread 57 that interacts with the screw thread 17 on the circumference of the jar 1. By turning the cage 54 with respect to the jar 1, the predetermined breaking point 4 can be pierced and the container can be opened and thus the liquid can be withdrawn.

Another embodiment is shown in FIG. 6. Here, the predetermined breaking point 4 lies in the region of the portion 61 to be welded.

Handling during withdrawal of the liquid takes place as follows:

If it is intended to withdraw the liquid with a set of injection instruments, the hollow needle is placed onto the marked point 30 of the septum 3, pierces therethrough and breaks through the predetermined breaking point 4 so as to reach the interior 10 of the container. Subsequently, as much liquid as needed is suctioned from the content of the container. Further liquid can be suctioned via the usual connector for standard needles.

It is also possible to work with special liquid withdrawal devices 5 as they have been described above.

The liquid withdrawal device 5 according to FIG. 2 is positioned at the marked point 30 so as to pierce the septum 3 and the predetermined breaking point 4. Thereby, a discharge channel 50 from the interior 10 of the container is opened, as a result of which liquid can flow into a jar that is not illustrated here. The filter in the transverse opening 53 allows air or gas bubbles to rise through the channel 50 into the interior 10 of the container.

It is also possible to feed gas pressure through the transverse opening 53 in order to push liquid out of the interior of the container. Gas supply can take place through a cannula into the interior 50 of the hollow needle 51 so as to provide for a clear separation of the flows within the hollow needle (not illustrated).

In the embodiments according to the FIGS. 3 to 5, the hollow needle 51 is pressed through the septum 3 by means of the guide device 54, and the predetermined breaking point 4 is broken open so as to get access into the interior of the container. Thereafter, the liquid is withdrawn via the channel 50 as described above.

In the case of hollow bodies 10 made from glass or other brittle materials, splinters can form when the point of the hollow needle breaks through the predetermined breaking point 4, which splinters can be caught by filter material. A filter fleece can be used in the channel 50, or the channel 50 is connected to a filter unit via which the liquid is delivered to the intended location.

In the above description, diverse measures and features of different embodiments of the container have been described. It is understood that these measures and features can also be used in combinations other than those described here so as to obtain further embodiments of the invention.

The invention claimed is:

1. A container for containing a liquid, comprising:

a hollow body having a wall with a bottom along a portion of the wall; and an elastomer septum, wherein a thickness-reduced section of the bottom of the wall of the hollow body has a reduced thickness relative to the rest of the bottom that provides a predetermined breaking point in which the thickness-reduced section is pierceable by the point of a hollow needle, and wherein the elastomer septum lies directly above the predetermined breaking point and is fixedly connected to the hollow body at the wall thereof.

2. The container for containing a liquid according to claim 1, wherein the thickness of the septum is in the range of 0.3 to 15 mm.

3. The container for containing a liquid according to claim 1, wherein the hollow body consists of plastic.

4. The container for containing a liquid according to claim 3, wherein said plastic comprises any of the materials from the group polyamide, in particular PA 6.6 or PA 12, cyclic olefin copolymers (COC), polypropylene and polyethylene.

5. The container for containing a liquid according to claim 1, wherein the hollow body consists of glass.

6. The container for containing a liquid according to claim 5, wherein the glass is selected from the glasses of the hydrolytic class 1 according to ISO 719 (DIN 12111) or from a class corresponding to this class with comparable properties.

7. The container for containing a liquid according to claim 1, wherein the thickness-reduced section is formed as a funnel-shaped dent or groove.

8. The container for containing a liquid according to claim 1, wherein the thickness-reduced section is formed as a thickness-reduced wall.

9. A container according to claim 1, the container being filled with liquid, wherein said hollow body comprises a jar and a cover which are welded or fused together so as to form an inner wall from a single material.

10. A package, comprising:

a container filled with liquid according to claim 9; and a liquid withdrawal device having a hollow needle for piercing the thickness-reduced section.

11. The package according to claim 10, further comprising a tube having a transverse opening therethrough, the hollow needle being inserted into the tube and having an interior, wherein the transverse opening communicates with the interior via a filter membrane in the transverse opening that is permeable to gases including air and impermeable to liquids.

12. The container according to claim 1, wherein the hollow body further includes a jar having an opening, and wherein the wall is a cover covering the opening of the jar.

13. A container for containing a liquid, comprising:

a hollow body having a wall; and an elastomer septum, wherein the wall of the hollow body includes a wall indentation that provides a predetermined breaking point in which the wall indentation is pierceable by the point of a hollow needle, wherein the elastomer septum lies directly above the predetermined breaking point and is fixedly connected to the hollow body at the wall thereof, and wherein the elastomer septum comprises any of the materials from the group of silicone, isobutyl rubber and neoprene.

14. The container for containing a liquid according to claim 13, wherein the thickness of the septum is in the range of 0.3 to 15 mm.

15. The container for containing a liquid according to claim 13, wherein the hollow body consists of plastic.

16. The container for containing a liquid according to claim 13, wherein the hollow body consists of glass.

17. The container for containing a liquid according to claim 13, wherein the wall indentation is formed as a funnel-shaped dent or groove.

18. A container according to claim 13, the container being filled with liquid, wherein said hollow body comprises a jar and a cover which are welded or fused together so as to form an inner wall from a single material.

19. The container according to claim 13, wherein the hollow body further includes a jar having an opening, and wherein the wall is a cover covering the opening of the jar.

20. A container for containing a liquid, comprising:

a hollow body having a wall; and an elastomer septum, wherein the wall of the hollow body includes a wall indentation that provides a predetermined breaking point in which the wall indentation is pierceable by the point of a hollow needle, and wherein the elastomer septum lies directly above the predetermined breaking point and is fixedly connected to the hollow body at the wall thereof.

21. The container for containing a liquid according to claim 20, wherein the thickness of the septum is in the range of 0.3 to 15 mm and the wall indentation is formed as a funnel-shaped dent or groove.

* * * * *